(12) United States Patent
Bisogno et al.

(10) Patent No.: US 7,244,767 B2
(45) Date of Patent: Jul. 17, 2007

(54) N-ACYLVANILLINAMIDE DERIVATIVES CAPABLE OF ACTIVATING PERIPHERAL CANNABINOID RECEPTORS

(75) Inventors: Tiziana Bisogno, Naples (IT); Francesco Della Valle, Padua (IT); Luciano De Petrocellis, Naples (IT); Vincenzo Di Marzo, Naples (IT); Gabriele Marcolongo, Padua (IT); Dominique Melck, Naples (IT)

(73) Assignees: Innovet Italia S.R.L., Milan (IT); Consiglio Nazionale Delle Richerche, Rome (IT)

( * ) Notice: Subject to any disclaimer, the term of this patent is extended or adjusted under 35 U.S.C. 154(b) by 0 days.

(21) Appl. No.: 10/949,322

(22) Filed: Sep. 27, 2004

(65) Prior Publication Data
US 2005/0065216 A1    Mar. 24, 2005

Related U.S. Application Data

(63) Continuation of application No. 09/787,764, filed as application No. PCT/EP99/06980 on Sep. 21, 1999, now abandoned.

(30) Foreign Application Priority Data
Sep. 24, 1998 (IT) .............................. MI98A2064

(51) Int. Cl.
*A61K 31/165* (2006.01)
*A61K 31/16* (2006.01)

(52) U.S. Cl. ...................... 514/616; 514/630
(58) Field of Classification Search ................ 514/616, 514/630
See application file for complete search history.

(56) References Cited

FOREIGN PATENT DOCUMENTS

| JP | 0613879 | 9/1994 |
|---|---|---|
| WO | WO 96/18391 | 6/1996 |

OTHER PUBLICATIONS

Morre, D.J. et al, Eur. J. Cancer, 1996, 32A(11), 1995-2003.*
West, A.R. Solid State Chemistry and its Applications, Wiley, 1988, pp. 358 and 365.*
Morre et al European Journal of Cancer, 1996, 32A(11), 1995-2003.*
Melck D et al.: "Unsaturated long-chain N-acyl-vanillyl-amides (N-AVAMs): vanilloid receptor ligands that inhibit anandamide-facilitated transport and bind to CB1 cannabinoid receptors." Biochemical and Biophysical Research Communications, Aug. 1999, 262 (1) 275-84.
Di Marzo V et al.: "Interactions between synthetic vanilloids and the endogenous cannabinoid system." FEBS Letters, Oct. 1998, 436 (3) 449-54.
Dray A.: "Neuropharmacological Mechanisms of Capsaicin and Related Substances" Biochemical Pharmacology, GB, Pergamon, Oxford, vol. 44, No. 4, Aug. 1992, pp. 611-61.
Winter J. et al.: "Characterization of resiniferatoxin binding sites on sensory neurons: Co-regulation of resiniferatoxin binding and capsaicin sensitivity in adult rat dorsal root ganglia." NEUROSCIENCE, (1993) 57/3 (747-757).
Morre D J et al.: "Capsaicin inhibits plasma membrane NADH oxidase and growth of human and mouse melanoma lines." European Journal of Cancer, (Oct. 1996) 32A (11) 1995-2003.
Database WPI Section Ch, Week 199318 Derwent Publications Ltd., London, GB; AN1993-149228 & JP05 086086 (Ogawa Koryo KK), Apr. 1993
Database WPI Section Ch, Week 199815 Derwent Publications Ltd., London, GB; AN1998-162352 & JP10 025237 (Kanebo Ltd), Jan. 1998.
Janusz, J.M. et al "Vanilloids. Analogs of Capsaicin with Antinociceptive and Antininflammatory Activity", Journal of Medicinal Chemistry, 1993, 36, 2592-2604.

* cited by examiner

*Primary Examiner*—Shaojia Anna Jiang
*Assistant Examiner*—Ganapathy Krishnan
(74) *Attorney, Agent, or Firm*—Nixon & Vanderhye P.C.

(57) ABSTRACT

The present invention relates to the use of N-acylvanillinamide derivatives capable of activating the peripheral receptor CB1 of cannabinoids. In particular, the present invention relates to the use of compounds of general formula (I)

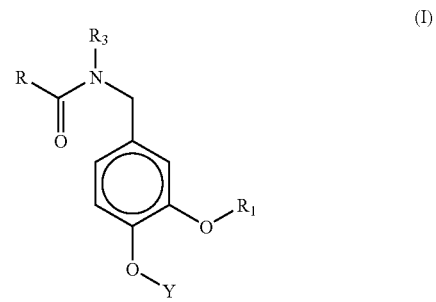

in which the meanings of R, $R_1$, $R_3$ and Y are as defined in the description, for the preparation of a medicinal product which is capable of activating the peripheral receptor CB1 of cannabinoids.

1 Claim, No Drawings

N-ACYLVANILLINAMIDE DERIVATIVES CAPABLE OF ACTIVATING PERIPHERAL CANNABINOID RECEPTORS

CROSS REFERENCE TO RELATED APPLICATION

This application is a continuation of application Ser. No. 09/787,764 filed Jul. 27, 2001 now abandoned which in turn is a §371 of PCT/EP99/06980 filed Sep. 21, 1999.

The present invention relates to the use of N-acylvanillinamide derivatives which are capable of activating the peripheral receptor CB1 of cannabinoids.

PRIOR ART

The hyperreactivity of certain cell lines (for example: mastocytes, basophils, glutamatergic neurons, dopaminergic neurons, lactotropic and mammotropic cells of the pituitary gland, etc.) and, consequently, the hyperreactivity of the tissues, including tumour tissues, influenced by the above-mentioned cell lines, is, in the light of the most recent scientific knowledge, considered to be the consequence of sensitization of the cells (generally nerve cells) involved in stimulating these cell lines.

These sensitization phenomena, mediated by the levels of specific effectors, are regulated by fine agonism/antagonism mechanisms in which Nerve Growth Factor (NGF) has recently been shown to play a key role.

It has recently been shown that NGF, taken up at the peripheral ends of sensitive fibres across the specific, high-affinity receptor trkA, is capable of acting on specific groups of sensitive neurons—capsaicin-sensitive neurons—and on the respective peripheral axons which innervate the tissues, causing a rapid and intense increase in the levels of the peptide transmitters substance P and CGRP (calcitonin gene-related peptide) [R. Levi Montalcini et al., (1996) TINS, 11: 514-520].

By means of this mechanism, the NGF produced, which is stored and abruptly released at the periphery—mainly in the resident mastocytes [A. Leon et al. (1994) Proc. Natl. Acad. Sci. U.S.A. 91: 3739-3743]—is capable of influencing the sensitivity of sensory neurons.

In addition, the huge volume of research recently produced has demonstrated effects of NGF on cell populations—both circulating and resident cells—which are generally known to be involved in maintaining specific pathological situations in a hyperreactive state.

In particular, local increases in the levels of NGF [A. Hamada et al. (1996) British J. Aematol., 93: 299-302; P. T. Manning et al. (1985) Brain Res., 340: 61-69; U. Otten et al. (1989) Proc. Natl. Acad. Sci. U.S.A., 86: 1059-1063; Y. Kannan et al. (1991) Blood, 77:1320-1325; A. Lambiase et al. (1997) J. Allergy Clin. Immunol., 100: 408-414; L. Bracci Laudiero et al. (1996) Neuroreport, 7: 485-488; H. Matsuda et al. (1991) J. Exp. Med., 174: 7-14; R. Levi Montalcini et al. (1977) Brain Res., 133: 358-366; A. Bruni et al. (1982) FEBS Letters, 138: 190-194; R. Paus et al. (1994) British J. Dermatol., 130: 174-180; C. Pincelli et al. (1997) J. Invest. Dermatol., 109: 757-764; Y. Susaki et al. (1996) Blood, 88: 4630-4637; J. Bienensthck et al. (1987) Int. Arch. Allergy Appl. Immunol., 82: 238-243; N. Mazurek et al. (1986) FEBS Letters, 198: 315-320; M. Tomioka et al. (1988) J. Allergy Clin. Immunol., 82: 599-607; M. Proesmans et al. (1997) Mol. Cell. Endocrinol., 134: 119-127; C. Missale et al. (1995) Endocrinology, 136: 1205-1213; S. Descamp et al. (1998) J. Biol. Chem., 273: 16659-16662; B. R. Pflug et al. (1995) Endocrinology, 136: 262-268; A. Angelsen et al. (1998) Scand. J. Urol. Nephrol., 32: 7-13; A. A. Geldof (1997) J. Cancer Res. Clin. Oncol., 123: 107-112] are capable of:

lowering, by means of a priming effect, the activation threshold of the circulating basophils and of the resident mastocytes;

increasing the cytotoxicity and the chemotaxis of eosinophils;

stimulating the phagocytosis, cytotoxicity and specific cytokine release of macrophages;

increasing the proliferation of keratinocytes;

activating the differentiation and proliferation of the B lymphocytes, as well as the production of antibodies by these lymphocytes;

stimulating the production of neuropeptides by the T lymphocytes;

inducing the chemotaxis of neutrophils;

stimulating the differentiation of the mastocyte precursors towards the connective phenotype;

increasing the number of lactotropic cells of the pituitary gland which incorporate [$^3$H]-thymidine and increasing the number of cells which express mRNA for prolactin;

stimulating the terminal differentiation and proliferation of mammotropic cells of the pituitary gland in the course of post-natal maturation;

stimulating the proliferation of breast tumour cells (MCF-7) but not the growth of normal breast epithelial cells (NBECs);

regulating the growth of human prostate epithelial cells;

stimulating the growth rate and invasive capacity of human prostate carcinoma cell lines (DU-145; PC-3; etc.).

Various studies have been published which demonstrate that large increases in the levels of NGF are associated with various pathologies of hyperreactive form, such as, for example:

chronic arthritis [L. Aloe et al. (1992) Arthritis Rheum., 35: 351-355]

multiple sclerosis [L. Bracci Laudiero et al. (1992) Neurosci. Lett., 147: 9-12]

lupus erythematosus [L. Bracci Laudiero et al. (1993) Neuroreport, 4: 563-565; L. Bracci Laudiero et al. (1996) Neurosci. Lett., 204: 13-16]

scleroderma [M. A. Tuberi et al. (1993) Clin. Exp. Rheumatol., 11: 319-322]

allergic pathologies and in particular urticaria syndrome, angioedema and asthma [S. Bonini et al. (1996) Proc. Natl. Acad. Sci. U.S.A., 93: 10955-10960]

keratoconjunctivitis [A. Lambiase et al. (1995) Invest. Ophthalmol. Vis. Sci., 36: 21-32]

parasitic infections [L. Aloe et al. (1994) Neuroreport, 5: 1030-1032; L. Aloe et al. (1996) Acta Neuropathol., 92: 300-305]

abstinence from alcohol and heroin [L. Aloe et al. (1996) Alcohol Clin. Exp. Res., 20: 462-465]

manifestations of psychological stress and anxiety [L. Aloe et al. (1994) Proc. Natl. Acad. Sci. U.S.A., 91: 10440-10444]

granuloma [R. Levi Montalcini et al. (1960) IV Int. Neurochem. Symp.]

psoriasis [S. P. Raychaudhuri et al. (1998) Acta Derm. Venereol., 78: 84-86]

The phenomenon of sensitization has been observed both at the peripheral level and in the central nervous system ("peripheral sensitization" and "central sensitization" respectively).

At the peripheral level, the phenomenon is due to the fact that by activating, for example, the nociceptors, which are normally at a high threshold, a lower level of stimulation becomes sufficient.

Again at the peripheral level, the sensitization phenomenon is capable of influencing the many delicate biological mechanisms in which substance P (SP) acts as an effector.

In particular, it is known [T. Lotti et al. (1995) J. Am. Acad. Dermatol., 33: 482-496; J. C. Ansel et al. (1996) J. Invest. Dermatol., 106: 198-204; M. Suzuki et al. (1995) Peptides, 16: 1447-1452; J. Luber-Narod et al. (1994) J. Immunol., 152: 819-824; H. P. Hartung (1998) Fed. Amer. Soc. Exp. Biol. Journal, 2: 48-51; G. Jancso (1985) Intern. J. Tiss. React., 7: 449-457; F. Shanahan (1986) Int. Arch. Allergy Appl. Immunol., 80: 424-426; I. Berczi (1996) Bailliére's Clin. Rheumat., 10: 227-257] that:

SP acts on the microvasal endothelium both directly by means of interaction with the specific NK1 receptor, and indirectly via contraction of the smooth muscle fibres and via the release of histamine by the mastocytes;

SP acts directly on mastocytes, giving rise to the phenomenon of degranulation, without, however, requiring extracellular $Ca^{2+}$;

SP induces the adhesion of leukocytes to the endothelium, presumably by means of mastocyte degranulation;

SP stimulates the synthesis of mediators which are not stored, such as leukotrienes;

SP specifically stimulates the mastocytic production and secretion of Tumour Necrosis Factor (TNF-α) in a concentration-dependent manner;

SP induces, in keratinocytes, the synthesis of interleukin-1 (IL-1) but not that of tumour necrosis factor (TNF-α) or interleukin-8 (IL-8);

SP induces the production and secretion of interleukin-8 (IL-8) in the microcirculatory endothelium;

SP increases the proliferation of the circulating T lymphocytes;

SP increases the synthesis of immunoglobulin A (IgA);

SP regulates the synthesis of cytokines in the monocytes (including γ-interferon);

SP induces infiltration of granulocytes into the skin, mediated by leukotriene B4;

SP stimulates the proliferation of fibroblasts, smooth muscle cells, keratinocytes and the endothelium, thus playing a key role in tissue repair processes;

SP increases the secretion of tumour necrosis factor (TNF-α) by the neuroglial cells after activation with lipopolysaccharides. This action of SP is mediated by astrocytes;

SP stimulates the release of prostaglandin E2 (PGE2) and of collagenase from rheumatoid synovyiocytes.

"Central sensitization" is due to the fact that, in the central nervous system, the increase in the levels of substance P and CGRP simulated by NGF in the central ends of sensitive neurons, gives rise to a prolonged "synaptic facilitation" in the spinal cord.

In practice, afferent sensory inputs into the spinal cord are capable of giving rise to pain sensations mediated by the NMDA glutamatergic receptors and by tachykinin receptors as a result of the increase in the release of excitatory amino acids and neuropeptides [C. J. Woolf (1983) Nature, 306: 686-688; P. Levi Montalcini et al. (1996) TINS, 11: 514-520].

At the level of pituitary gland structures which are responsible for the synthesis of prolactin and which are known to be under dopaminergic and serotoninergic central control activated by psychogenic stimuli, NGF acts as an inducer of prolactin production, given its capacity to bring about a change in the phenotype towards cells capable of synthesizing prolactin [R. Levi Montalcini et al. (1996) TINS, 11: 514-520].

In the presence of tumour cells which express prolactin receptors, an excessive increase in the level of the hormone can be a potent proliferative stimulus to these cells. In particular, it is known that:

breast tumour cells express prolactin receptors, respond to treatment with prolactin and synthesize their own prolactin [W. E. Simon et al. (1985) J. Clin. Endocrinol. Metab. 60: 1243-1249; E. Giusburg et al. (1995) Cancer Res. 55: 2591-2595; C. V. Clevenger et al. (1995) Am. J. Athol. 146: 695-705; R. P. C. Shiu (1985) J. Biol. Chem. 260: 11307-11313].

As with normal human prostate cells and human prostate cells from individuals suffering from benign prostate hypertrophy, human prostate carcinoma cells express the prolactin receptor [M. Fakete et al. (1989) Prostate, 14: 191-208]. The presence of the specific prolactin receptor on cells from human prostate biopsies has been studied as a prognostic indicator of a prostate tumour [M. A. Blankenstein et al. (1988) Scand. J. Urol. Nephrol. Supl., 107: 39-45]. By means of the interaction of prolactin, from the bloodstream, with the specific receptors present on prostate cells, it is involved in the development of prostate tumours in man [L. Romero et al. (1991) Acta Urol. Esp., 15: 503-509]. To demonstrate this involvement, it has been shown that it is possible to obtain a decrease in the effect of prolactin on promoting the growth of the prostate tumour by reducing the total number of prolactin receptors [T. Kadar et al. (1988) Proc. Natl. Acad. Sci. U.S.A., 85: 890-894].

It is also known that NGF and prolactin are co-synthesized and co-released by specific populations of cells in the pituitary gland [C. Missale et al. (1994) Endocrinology, 135: 290-298].

For its part, anandamide, which is recognized as being the endogenous ligand of the cannabinoid receptor CB1, is capable of modifying the levels of prolactin in the serum [J. Weidenfeld et al. (1994) Neuroendocrinology 59: 110-112; T. Wenger et al. (1995) Life Sci. 56: 2057-2063; J. Romero et al. (1994) Neuroendocrinol. Letts. 16: 159-164].

Furthermore, it is known that many tumours overexpress NGF or its receptor [S. Cohen et al. (1954) Proc. Natl. Acad. Sci. U.S.A., 40: 1014-1018; P. G. Chesa et al. (1998) J. Histochem. Cytochem., 36: 383-389; M. D. Simone et al. (1993) 34$^{th}$ Congress on Haematology, Naples 5-8 October]. In particular, it is known that receptors which have both low and high affinity for NGF are expressed at the stromal level in human prostate tissue [T. Kadar et al. (1988) Proc. Natl. Acad. Sci. U.S.A., 85: 890-894].

In any case, the presence of cannabinoid receptors CB1 on breast tumour cells or on prostate carcinoma cells was not known hitherto [R. G. Pertwee (1997) Pharmacol. Ther. 74: 129-180).

It is only very recently that it has been found that anandamide and stable analogues thereof are capable of reducing the cell proliferation of human tumour lines of breast cancer by means of a specific interaction with the cannabinoid receptor CB1; this effect is clearly prolactin-mediated [L. De Petrocellis (1998) Proc. Natl. Acad. Sci. U.S.A., 95: 8375-8380].

The peripheral cannabinoid receptor CB1 is expressed by neurons which are substance P/capsaicin-sensitive [AG.

Hommann et al. (1997) Abstract Soc. Neurosci. 23: 1954] and can be measured [J. D. Richardson et al. (1998) J. Neurosci. 18: 451-457].

In these endings, stimulation of the peripheral cannabinoid receptor CB1; inhibits the neurosecretion of substance P and CGRP [J. D. Richardson et al. (1998) Pain 75: 111-119].

In practice, stimulation of the peripheral cannabinoid receptor CB1 is opposed by the increase in the levels of substance P and CGRP induced by NGF.

As a result, stimulation of the peripheral cannabinoid receptor CB1 brings about—on the endings of sensitive fibres—regulation of both the peripheral and central sensitization induced by NGF.

In confirmation of this, it has been shown that anandamide—the endogenous ligand of the cannabinoid receptor CB1—is capable of inhibiting both the induction and the persistence of thermal hyperalgesia induced by carrageenan. The effect is antagonized by the specific CB1 receptor antagonist known as SR 141716A [J. D. Richardson et al. (1998) Pain 75: 111-119].

The cannabinoid receptor CB1 is present in many nerve structures of the hypothalamo-hypophyseal axis [J. J. Fernandez-Ruiz et al. (1997) Biochem. Pharmacol., 53: 1919-1927—T. Wenger et al. (1997) Biochem. Biophys. Res. Comun., 273: 724-728].

Moreover, it has recently been demonstrated that the cannabinoid receptors CB2 are located on the mastocytes [L. Facci et al. (1995) Proc. Natl. Acad. Sci. U.S.A., 92: 3376-3380] and that activation of these receptors by means of the endogenous ligand palmitoylethanolamine (PEA) and analogues (ALIAmides) is capable of inhibiting the mastocytic activation induced by substance P [L. Aloe (1993) Agents Actions, 39: C145-C147].

It has also been demonstrated that the simultaneous local administration of anandamide and palmitoylethanolamine gives rise to a highly synergistic effect which can be antagonized with antagonists specific for the respective receptors [A. Calignano et al. (1998) Nature, 394: 277-281]. This is further proof of the fact that, besides having different structures and being capable of accommodating different types of ligands, the two receptors are capable of mediating various patterns of effects or of causing the same effect, but acting by a different mechanism.

It is thus clear that the search for molecules which act selectively on the peripheral cannabinoid receptor CB1 is an objective of great pharmacological interest.

SUMMARY OF THE INVENTION

The present invention is based on the possibility of pharmacologically antagonizing—by means of the functional stimulation of the peripheral cannabinoid receptors CB1, which is obtained, surprisingly, with a family of N-acylvanillinamide (N-AVAM) compounds—the effects induced by supramaximal levels of NGF, which facilitate the phenomenon of central and peripheral sensitization, as well as phenomena of hormone-dependent hyperproliferation of tumour cells such as, for the purposes of non-limiting illustration, those of human breast and prostate carcinoma.

The pharmacological use of these molecules opens new and unexpected therapeutic avenues in all pathologies characterized by a high degree of cellular and tissue hyperreactivity mediated by supramaximal levels of NGF.

We have discovered, surprisingly, that the said N-acylvanillinamide (N-AVAM) molecules are pharmacologically capable of functionally stimulating the peripheral cannabinoid receptor CB1 with an affinity which is comparable to that of anandamide.

From these unforeseeable results, we have discovered that N-AVAM molecules are capable of controlling the hyperreactivity of specific cell and tissue lines by means of regulating the central and peripheral sensitization of afferent sensitive fibres.

We have also demonstrated for the first time that the effect of N-AVAM molecules on specific consequences of cellular and tissue hyperreactivity can be synergized by N-acylamide molecules (ALIAmides) acting on the cannabinoid receptor CB2 expressed by mastocytes.

Finally, we have discovered, unexpectedly, that the exogenous administration of N-AVAM molecules is capable of inhibiting, in a dose-dependent manner and again by means of stimulation of the cannabinoid receptor CB1, the proliferation of tumour cells, which is dependent on the presence of the prolactin (PRL) receptor, such as, for example, human breast tumour cells and human prostate carcinoma cells, and that this inhibition is significantly synergized by the simultaneous exogenous administration of agonist molecules which are functionally active on the receptor CB2.

Molecules of N-acylvanillinamide structure are known and have been described as having agonist activity on the receptor CB2 (WO 96/18391). In contrast, we have found that these molecules have selective activity on the peripheral cannabinoid receptor CB1.

DESCRIPTION OF THE INVENTION

A subject of the present invention is the use of derivatives of general formula (I):

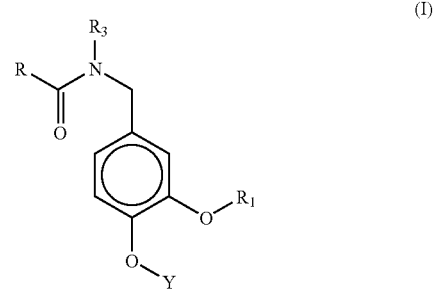

in which:
a) $R_1$ is chosen from the group comprising hydrogen, linear or branched, saturated or unsaturated C1-C10 alkyl, C3-C7 cycloalkyl or C7-C10 arylalkyl;
b) Y is chosen from the group comprising:
b1. hydrogen;
b2. a group of formula

in which —$R_8$— is a saturated, linear or branched C2-C6 alkylene radical and M is chosen from the group comprising —$NH_2$, acylamine, —$NHR_6$, —$NR_4R_5$, —$^{\oplus}NR_4R_5R_6$ $Z^-$, which may be identical or different, and $R_4$, $R_5$ and $R_6$, which may be identical or different, can be C1-C7 alkyl, alkenyl or arylalkyl radicals or $R_4$, and $R_5$ can form a cycloalkyl radical optionally containing hetero atoms such as —O— and —$NR_{12}$—, in which $R_{12}$ is chosen from hydrogen and an alkyl, aralkyl or hydroxyalkyl radical preferably chosen from —CH$_3$, —C$_2$H$_5$, —CH$_2$—C$_6$H$_5$, and —CH$_2$CH$_2$OH and Z$^-$ is as defined below; b3. a group of formula

in which R$_9$ is a saturated or monounsaturated, linear or branched C1-C10 alkyl radical, or a cycloalkyl, arylalkyl or heterocyclic radical optionally substituted with one or more —OH, —COOH, —SO$_3$H, —NH$_2$, —NHR$_6$, —NR$_4$R$_5$, —⊕NR$_4$R$_5$R$_6$ Z$^-$ groups, which may be identical or different, the said groups R$_4$, R$_5$, and R$_6$, which may be identical or different, being chosen from the group comprising C1-C7 alkyl, alkenyl and aralkyl radicals, or R$_4$ and R$_5$ can form a cycloalkyl radical which can comprise one or more hetero atoms such as —O— and —NR$_{12}$—; in which R$_{12}$ is chosen from hydrogen and an alkyl, aralkyl or hydroxyalkyl radical preferably chosen from —CH$_3$, —C$_2$H$_5$, —CH$_2$—C$_6$H$_5$ and —CH$_2$CH$_2$OH and Z$^-$ is as defined below, b4. a —PO$_3$H$_2$, —SO$_3$H, or —P(OH)$_2$ group, b5. a monosaccharide residue linked by an α- or β-glycoside bond, b6. a group of formula

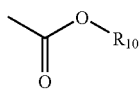

in which R$_{10}$ is a linear or branched, saturated or unsaturated C1-C10 alkyl or alkenyl radical, or a cycloalkyl or aralkyl radical optionally containing from 1 to 5 identical or different hetero atoms chosen from —S—, —O— and —N—, and optionally substituted with one or more —OH, —NH$_2$, —NH—CO—CH$_3$, —COOH, >C=O, H$_2$N—CO—NH—, NH=C(NH$_2$)—NH—, —NO$_2$, —OCH$_3$, —Cl, —Br, —F, -J, —OPO$_3$H$_2$, —OPO$_2$H$_2$, —OSO$_3$H, —OSO$_3$H, —SH, —SCH$_3$, —S—S—, —NHR$_6$, —N R$_4$R$_5$, —⊕NR$_4$R$_5$R$_6$ Z$^-$ groups, which may be identical or different, in which R$_4$, R$_5$ and R$_6$, which may be identical or different, can be C1-C7 alkyl, alkenyl or aralkyl radicals or R$_4$ and R$_5$ can form a cycloalkyl radical comprising one or more hetero atoms such as —O— and —NR$_{12}$—, in which R$_{12}$ is chosen from hydrogen and an alkyl, aralkyl or hydroxyalkyl radical preferably chosen from —CH$_3$, —C$_2$H$_5$, —CH$_2$—C$_6$H$_5$ and —CH$_2$CH$_2$OH and Z$^-$ is as defined below, c) R$_3$ is chosen from the group comprising hydrogen and linear or branched alkyl;

d) R is:

d1. carboxyl, —COOR$_7$, saturated or unsaturated cycloalkyl, polycyclic alkyl, aryl, heteroaryl, arylalkyl or C1-C35 alkyl, which is saturated or unsaturated with 1 to 6 double bonds, linear or branched and unsubstituted or substituted with one or more residues chosen from the group comprising carboxyl, —COOR$_7$, hydroxyl, alkoxy, O-acylhydroxy, ketoalkyl, nitro, halo, —SH, alkylthio, alkyldithio, amino, mono- and dialkylamino, N-acylamino, —$^+$NR$_4$R$_5$R$_6$Z$^-$, in which R$_4$, R$_5$ and R$_6$, which may be identical or different, are chosen from the group comprising C1-C7 alkyl, C1-C7 alkenyl and arylalkyl and Z$^-$ can be the anion of a biologically compatible inorganic or organic acid preferably chosen from hydrochloric acid, sulphuric acid, phosphoric acid, methanesulphonic acid, benzenesulphonic acid, p-toluenesulphonic acid, acetic acid, succinic acid, fumaric acid, lactic acid, gluconic acid, citric acid, glucuronic acid, maleic acid and benzoic acid;

d2. a group of formula

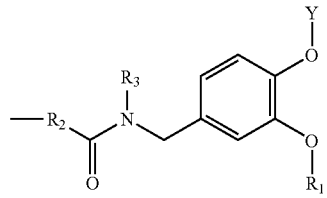

in which R$_1$, R$_3$ and Y have the meanings given above and R$_2$ can be a single bond or a linear-or branched, saturated or unsaturated C1-C34 alkylene radical containing from 1 to 6 double bonds, a saturated or unsaturated cycloalkylene radical, an aryl, aralkyl or heterocyclic diradical, which is unsubstituted or substituted with one or more residues chosen from the group comprising carboxyl, —COOR$_7$, hydroxyl, alkoxy, O-acylhydroxy, alkylketo, nitro, halo, —SH, alkylthio, alkyldithio, amino, mono- and dialkylamino, N-acylamino, saturated or unsaturated cycloalkyl, aryl and heteroaryl; in which R$_7$ is a linear or branched C1-C20 alkyl group or an aralkyl group, enantiomers and diastereoisomers of the compounds of formula (I) and mixtures thereof, salts of the compounds of formula (I) with pharmaceutically acceptable acids and bases, and solvates thereof, for the preparation of a medicinal product with agonist activity on the peripheral receptor CB1 of cannabinoids.

When R is an alkyl group, it is preferably a C6-C19 alkyl.

R$_1$ is preferably a C1-C7 alkyl group, in particular methyl, ethyl or isopropyl, or an allyl or benzyl group.

When R$_8$ is an alkyl group, it is preferably a C1-C4 alkyl.

When R$_8$ is an acylamino group, it is preferably chosen from acetylamino, benzoylamino, monosuccinylamino and monoglutarylamino.

When R$_9$ is an alkyl group, it is preferably a C1-C7 alkyl.

R$_4$, R$_5$ and R$_6$ are preferably identical and are methyl.

When Y is a saccharide group, it is preferably a mono-, di- or trisaccharide in which the hydroxyl groups in these saccharide groups are optionally esterified with acyl, sulphate or phosphate groups, or are replaced with one or more amine groups, optionally N-acylated amine groups.

When R$_3$ is an alkyl group, it is preferably a C1-C5 alkyl.

When R$_2$ is an alkylene group, it is preferably a saturated or monounsaturated C6-C12 alkylene.

R$_7$ is preferably a C1-C5 alkyl.

In the meanings of R, the terms "O-acylhydroxy" and "N-acylamino" preferably mean a C2-C5 O-acylhydroxy or C2-C5 N-acylamino.

Within the meanings of R, the term "alkoxy" preferably means a C1-C5 alkoxy.

Within the meanings of R, the term "mono- and dialkylamino" preferably means mono- and di(C1-C5)alkylamino, respectively.

Compounds of formula (I) which are particularly preferred for the use according to the present invention are those in which:

R$_1$ is methyl;

Y is hydrogen or a saccharide group chosen from D- and L-ribose, D- and L-glucose, D- and L-galactose, D- and L-mannose, D-fructose, D- and L-glucosamine, D-galactosamine, D-mannosamine, glucuronic acid, sialic acid, N-acetyl-D-glucosamine, N-acetyl-D-galactosamine, N-acetyl-D-mannosamine; or aminoethyl, dimethylaminoethyl, trimethylaminoethyl; or methylcarbonyl, phenylcarbonyl, pyridinocarbonyl, trimethoxyphenylcarbonyl, hemisuccinoyl, aminomethylcarbonyl, aminopropyl-carbonyl, dimethylaminomethylcarbonyl, trimethylaminomethylcarbonyl, sulphonophenylcarbonyl; or phosphate, sulphonate; or ethyloxycarbonyl, benzyloxycarbonyl, isobutyloxycarbonyl, dimethylaminopropyloxycarbonyl, trimethylaminoethyloxycarbonyl;

$R_3$ is hydrogen;

R is as defined above.

Compounds of formula (I) which are more particularly preferred are those in which R or $R_2$, together with the terminal —CO— groups to which they are attached, are, respectively, mono- or diacyl radicals of an acid chosen from the group comprising palmitic acid, arachidonic acid, oxalic acid, fumaric acid, maleic acid, azelaic acid, succinic acid, traumatic acid, muconic acid, cromoglycolic acid, tartaric acid, aspartic acid, glutamic acid, oleic acid, lauric acid, myristic acid, stearic acid, D- or L-lipoic acid, L-carnitine, L-acetylcarnitine and tropic acid.

The expression "pharmaceutically acceptable acids" means, for example, hydrochloric acid, hydrobromic acid, sulphuric acid, phosphoric acid, acetic acid, lactic acid, gluconic acid, citric acid, glucuronic acid, fumaric acid, maleic acid or benzoic acid.

The expression "pharmaceutically acceptable bases" means, for example, hydroxides of alkali metals and alkaline-earth metals or transition metals, such as, for example, zinc, ammonium, di- or trialkylamine, tetraalkylammonium, N-(2-hydroxyethyl)dimethylammonium, choline or amino acids such as lysine.

The expression "enantiomers and diastereoisomers of the compounds of formula (I) and mixtures thereof" is intended also to include the related racemates and racemic mixtures.

A further subject of the present invention is compounds of formula (I) in which Y is a saccharide group.

Preparation of the Compounds of Formula (I)

The compounds of formula (I) can be prepared by known methods, such as those described in the published PCT patent application WO 96/18391 (LIFEGROUP S.p.A.), which is incorporated herein by reference.

In particular, the synthesis of mono- and dicarboxamides with amines of vanillinamine structure can be carried out according to one of the general schemes below:

Scheme Ia for monoamides

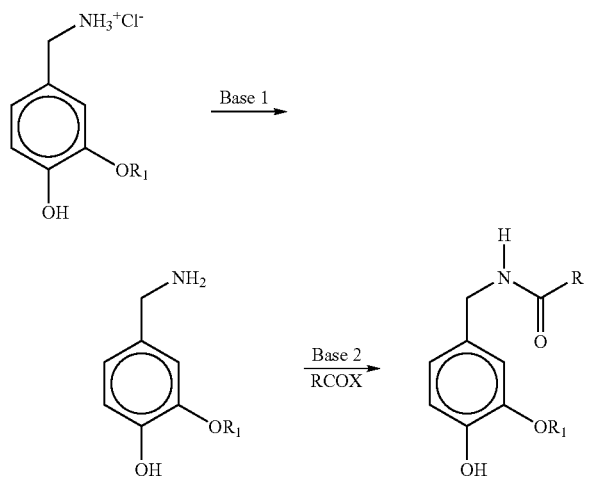

Scheme Ib for diamides

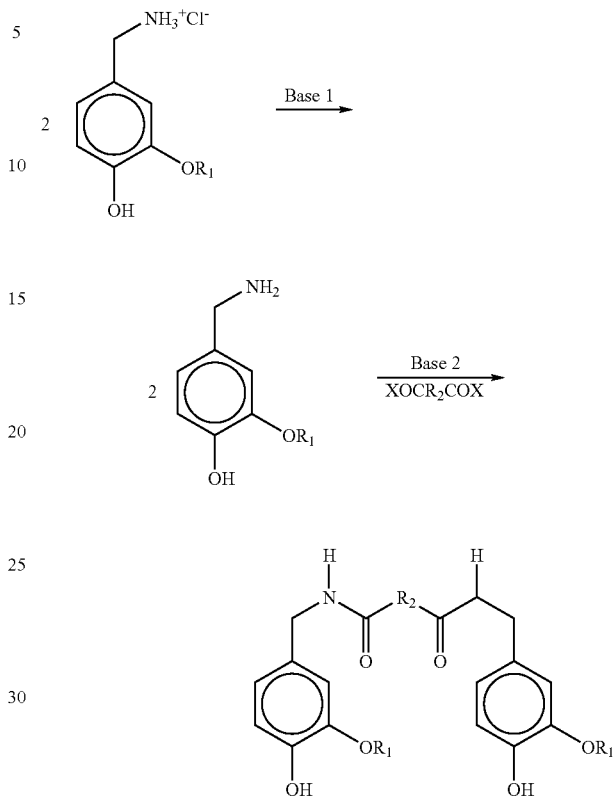

Base 1 and Base 2, which may be identical or different, can be chosen from common organic and inorganic bases and preferably, but without any limitation, from $Na_2CO_3$, $NaHCO_3$, $K_2CO_3$, $KHCO_3$, $MgCO_3$, NaOH, KOH, $Li_2CO_3$, LiOH, $Ca(OH)_2$, $Ba(OH)_2$, trimethylamine, triethylamine, tributylamine, 4-methylmorpholine, tetramethylammonium hyroxide, tetrabutylammonium hydroxide, pyridine and picoline.

R-COX and XOC—$R_2$—COX are reactive derivatives of carboxylic acids such as halides, esters, anhydrides and preferably, but without any limitation, X in this case can be —Cl, —Br, —OCH$_3$, —OC$_2$H$_5$, —O—CH$_2$—CH$_2$—O—C$_2$H$_5$, —O—C$_6$H$_4$—NO$_2$, —O—CH$_2$—CF$_3$, —O—CO—O—C$_2$H$_5$, —O—CO—O—C(CH$_3$)$_3$, —O—CO—O—CH$_2$—CH(CH$_3$)$_2$, —O—CO—O—CH$_2$—C$_6$H$_5$,

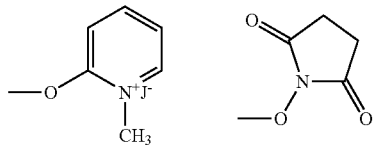

The reactions given in Schemes Ia and Ib can be carried out in the common solvents used in chemical synthesis and preferably, but without any limitation, in water, dimethyl sulphoxide, dimethylformamide, dimethylacetamide, diethylacetamide, N-methyl-pyrrolidone, pyridine, tetrahydrofuran, methyltetrahydrofuran, tert-butyl methyl ether, diisopropyl ether, diethyl ether, ethyl acetate, methyl acetate, butyl acetate, toluene, petroleum ether, acetone, xylene, methyl ethyl ketone, methyl isobutyl ketone, acetonitrile, propionitrile, 1,2-dichloroethane, dichloromethane, chloroform, 1,1,2-trichloroethylene, 1,1,1-trichloroethane, 1,2-dimethoxyethane, cyclohexane or mixtures thereof.

The reactions given in Schemes Ia and Ib can be carried out at temperatures of between −35° C. and +100° C. and preferably between −20° C. and +40° C. for a time ranging between 10 min and 48 h and preferably between 30 minutes and 6 h.

When the carboxylic acid is reacted in free form, the reaction will be carried out at high temperatures or in the presence of coupling agents such as, for example, dicyclohexylcarbodiimide or derivatives thereof.

When groups which might influence the coupling reaction are present on the amine or carboxylic substrate, such as, for example, hydroxyl, amino or carboxyl groups, these groups may be protected using suitable protecting groups known to those skilled in the art.

The compounds of formula (I) in which Y is a saccharide group can be prepared from the corresponding compounds in which Y is hydrogen, according to known reactions, such as, for example, those described in the published PCT patent application WO 95/25736 (LIFEGROUP S.p.A.).

In particular, the synthesis of the glycoside derivatives claimed with the definition of the groups Y is carried out by coupling the monosaccharide residues with the amides, obtained according to Schemes Ia and Ib, using methods commonly employed in the chemical synthesis of —O-glycosides at the laboratory and/or industrial production level, and preferably, but without any limitation, according to the scheme given below.

Scheme II for the synthesis of glycosides:

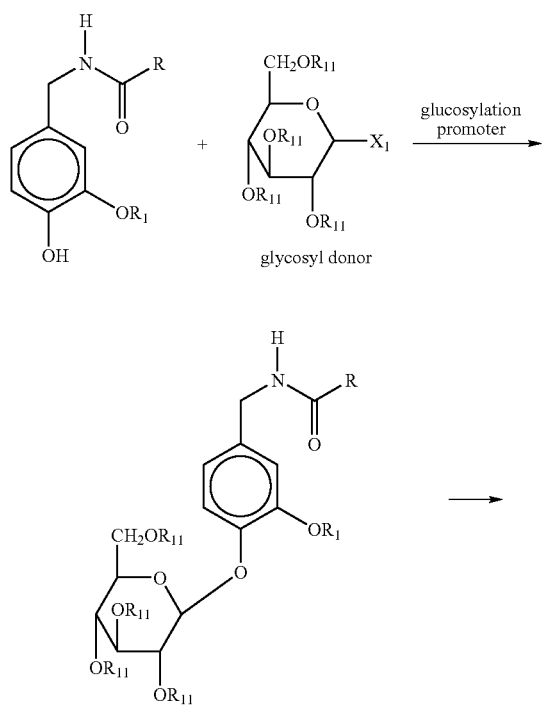

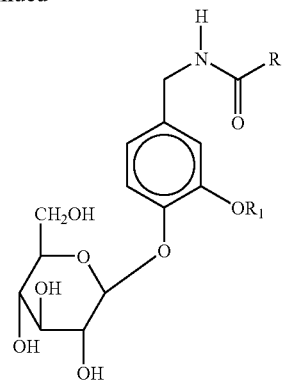

The glycosylation reactions are carried out at temperatures of between −80° C. and +60° C. and preferably between −30° C. and +20° C. in polar aprotic solvents and preferably, but without any limitation, in acetonitrile, nitromethane, tetrahydrofuran, methyltetrahydrofuran, dichloromethane, propionitrile, diethyl ether, diisopropyl ether, dimethoxyethane, 1,1,1-trichloroethane, acetone or mixtures thereof.

The glycosyl donor is a monosaccharide derivative which needs to be linked to the amide in which $R_{11}$ represents a protecting group for the OH groups preferably, but without any limitation, chosen from acetyl, benzyl and benzoyl. X represents a leaving group; in this case, X is preferably, but without any limitation, —Cl, —Br, —S—$CH_3$, —S—$C_2H_5$, —S—CS—O—$C_2H_5$, trichloroacetamidate or acetate.

The glycosylation promoter is preferably, but without any limitation, chosen from silver salts such as silver sulphate, carbonate, perchlorate, salicylate or trifluoromethanesulphonate or mixtures of salts such as $SnCl_4$—$AgClO_4$, $BiCl_3$—$AgClO_4$, $SbCl_3$—$AgClO_4$ optionally combined with iodosobenzene or tin(II) trifluoromethane-sulphonate, trifluoro-methanesulphonic acid, N-iodo-succinimide combined with trifluoromethanesulphonic acid, trimethylsilyl trifluoromethanesulphonate or boron trifluoride etherate.

The α-glycoside derivatives which cannot be obtained in satisfactory yield by direct glycosylation can be obtained from the corresponding β-glycosides by anomerization reaction using, for example, a reagent system consisting of magnesium bromide ethyl etherate and titanium tetrahalide [Chemistry Letters (1997), 7:625-626].

The protecting groups $R_{11}$ can readily be removed after the glycosylation reaction, for example by hydrolysis or hydrogenolysis: the acetate group can be removed at room temperature in anhydrous methanol or ethanol in the presence of catalytic amounts of an alkoxide, while the benzyl and benzoyl groups can be removed, respectively, by treatment with $H_2$ gas in the presence of catalysts such as Pd/C or by electrolytic reduction in solvents such as alcohols or organic acids.

The syntheses of the ester and carbonate derivatives claimed with the definition of the groups Y are carried out starting with the amides obtained according to Schemes Ia and Ib, preferably, but without any limitation, according to the general schemes below:

Scheme IIIa for the synthesis of esters

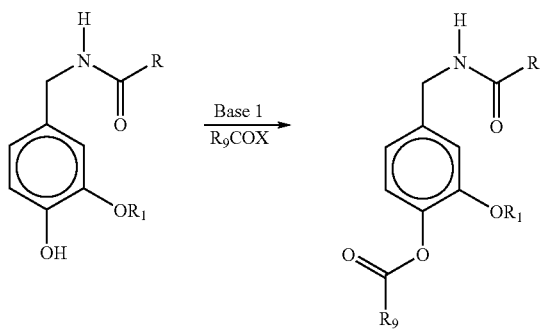

Scheme IIIb for the synthesis of carbonates

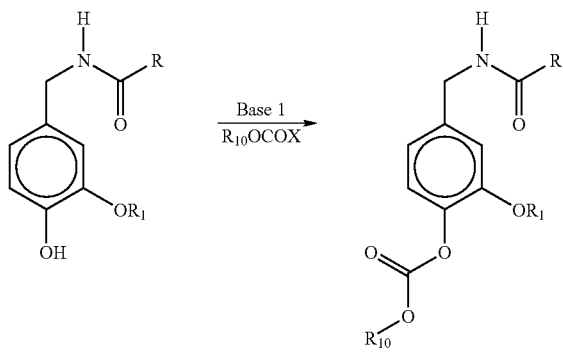

Base 1 has the meaning already given for Schemes Ia and Ib.

$R_9$—COX is the reactive derivative of a carboxylic acid and preferably, but without any limitation, a halide or an anhydride;

$R_{10}$—O—CO—X is a haloformate and preferably a chloroformate;

both $R_9$ and $R_{10}$ can bear protected functional groups which can be conveniently deprotected to give the final reaction product, or can bear reactive functional groups which can be used for further substitutions in order to obtain the desired final product.

The reactions given in Schemes IIIa and IIIb are carried out in solvents selected from those already described for the reaction in Schemes Ia and Ib under analogous time and temperature conditions.

Biological Activity

The compounds of the invention were studied using biochemical tests, in vitro and in vivo, described in the biological examples below. The compounds are identified by means of the example number given in the subsequent section of chemical examples.

EXAMPLE A

Effect of N-AVAM Molecules on the Binding of Synthetic Ligands of the Cannabinoid Receptor CB1

Method:

Mouse neuroblastoma cells N18TG2 which selectively express the cannabinoid receptor CB1 and rat leukaemia basophil cells RBL-2H3+ which selectively express the cannabinoid receptor CB2 were used. The cells were cultured as described previously [L. Faci et al. (1995) Proc. Natl. Acad. Sci. U.S.A., 92: 3376-3380; T. Bisogno et al. (1997) J. Biol. Chem., 272: 3315-3323]. [$^3$H]SR141716A (55 Ci/mmol) was supplied by Amersham; [$^3$H]WIN55, 212-2(43 Ci/mmol) was supplied by NEN. The binding tests were carried out with membranes of the said cells resuspended in 50 mM pH 7.0 Tris buffer; 2.5 mM mgCl$_2$; 0.8 mM EDTA; 0.05% bovine serum albumin (BSA); 0.01% ethanol and in the presence of 100 µM phenylmethylsulphonyl fluoride (PMSF; sigma) using 300 pM of [$^3$H]SR141716A and [$^3$H]WIN55,212-2, respectively, as ligand.

The membranes were incubated for 90 min at 30° C., filtered on glass microfibre filters (GFC-Whatman) and the radioactivity was measured by liquid scintillation. The specific binding was calculated using either 10 µM SR141716A or 10 µM HU-210 (obtained from Prof. R. Mechoulam, Hebrew University Jerusalem). The Ki values were calculated using the Chang-Prusoff equation and expressed as concentration µM.

Results:

| Test compound | CB1 receptor N18TG2 + cells [$^3$H]SR141716A ligand | CB2 receptor RBL-2H3 + cells [$^3$H]WIN55, 212-2 ligand |
|---|---|---|
| Compound of Example 1 | 1.64 ± 0.36 | >15 µM |
| Compound of Example 2 | 1.75 ± 0.35 | >15 µM |
| Compound of Example 3 | 1.50 ± 0.29 | >15 µM |
| Compound of Example 4 | 1.20 ± 0.28 | >15 µM |
| Capsaicin | >10 µM | >15 µM |
| Anandamide | 1.91 ± 0.31 | 0.03 ± 0.0029 |
| N-palmitoylethanolamine | >10 µM | 0.001 ± 0.0006 |

EXAMPLE B

Effect of N-AVAM Molecules on the Stimulation of Cyclic AMP (c-AMP) by Forskolin Method:

The tests were carried out with the aim of checking whether or not the binding of the N-AVAM molecules to the receptor CB1 had any functional significance. The c-AMP assays were carried out on confluent N18TG2 cells in 6-well petri dishes (Falcon); the cells were stimulated for 10 min at 37° C. with 1 µM forskolin (Fluka) in 400 µl of serum-free medium containing 20 mM Hepes, 0.1 mg/ml of BSA and 0.1 mM 1-methyl-3-isobutylxanthine (Sigma) and either ethanol or anandamide or N-AVAM molecules plus SR141716A. After incubation, the cells were extracted and the c-AMP levels were evaluated using a suitable kit from Amersham according to the manufacturer's procedure. The data are expressed as IC$_{50}$, in µM.

Results:

| Test compound | N18TG2 cells IC$_{50}$, µM |
|---|---|
| Anandamide | 3.2 |
| Compound of Example 1 | 1.6 |
| Compound of Example 1 + SR141716A (0.5 µM) | >20.0 |

-continued

| Test compound | N18TG2 cells IC$_{50}$, µM |
|---|---|
| Compound of Example 2 | 1.8 |
| Compound of Example 3 | 1.3 |

EXAMPLE C

Effect of N-AVAM Molecules on the Proliferation of Human Breast Carcinoma Cells

Method:

Human breast carcinoma cells MCF-7, EFM-19 and T-47D were used. The cells were cultured and the tests were carried out as described previously [materials and methods L. De Petrocellis et al. (1998) Proc. Natl. Acad. Sci. U.S.A., 95: 8375-8380]. The activity with respect to the proliferation of the tumour cells was evaluated on the basis of the incorporation of [$^3$H]-thimidine. The results are expressed as IC$_{50}$ in µM.

Results:

| Test compound | Cell MCF-7 | EFM-19 IC$_{50}$, µM | T-47D |
|---|---|---|---|
| Anandamide | 0.5 | 1.5 | 1.9 |
| Compound of Example 1 | 1.6 | 0.7 | 1.6 |
| Compound of Example 2 | 2.1 | 1.0 | 0.8 |
| Compound of Example 3 | 0.4 | 0.5 | 0.3 |

EXAMPLE D

Effect of N-AVAM Molecules on the Proliferation of Human Prostate Carcinoma Cells Method:

Human prostate carcinoma cells DU145 were used. The cells were cultured as described previously [materials and methods T. Janssen et al. (1996) Cancer, 77: 144-149].

The cells were then incubated in 96-well plates with Eagle's Minimal Essential Medium (MEM) supplemented with 10% foetal calf serum free of endogenous steroids. After 24 hours, the medium was removed and replaced with a medium containing prolactin (PRL) (1 mIU/ml of medium). The layer of cells was trypsinized and the cells were counted by haemocytometry.

The results are expressed as IC$_{50}$ in µM.

Results:

| Test compound | DU-145 cells IC$_{50}$, µM |
|---|---|
| Anandamide | 0.5 |
| Anandamide + SR141716A (0.5 µM) | >20.0 |
| Compound of Example 1 | 0.2–0.3 |

EXAMPLE E

Synergistic Effect of Aliamide Molecules (PEA) on the Antiproliferative Activity of Anandamide (Table A) and of N-AVAM Molecules (Table B) in Human Breast Carcinoma Cells Method:

Human breast carcinoma cells EFM-19 were used. The test was carried out as indicated in Example C above.

Results:

TABLE A

| Test compound | Proliferative activity % |
|---|---|
| Control (EFM-19) | 100 |
| Anandamide (1.0 µM) | 84 |
| PEA (1.0 µM) | 100 |
| PEA (2.5 µM) | 100 |
| PEA (5.0 µM) | 100 |
| PEA (10 µM) | 100 |
| Anandamide (1.0 µM) + PEA (1.0 µM) | 81 |
| Anandamide (1.0 µM) + PEA (2.5 µM) | 69 |
| Anandamide (1.0 µM) + PEA (5.0 µM) | 60 |
| Anandamide (1.0 µM) + PEA (10 µM) | 55 |

PEA IC$_{50}$ = 2.5 µM

TABLE B

| Test compound | Proliferative activity % |
|---|---|
| Control (EFM-19) | 100 |
| Compound of Example 1 (1.0 µM) | 60 |
| Compound of Example 1 (1.0 µM) + PEA (5.0 µM) | 10 |
| Compound of Example 3 (0.5 µM) | 70 |
| Compound of Example 3 (1.0 µM) | 43 |
| compound of example 3 (0.05 µM) + PEA (5.0 µM) | 61 |
| Compound of Example 3 (0.1 µM) + PEA (5.0 µM) | 50 |
| Compound of Example 3 (0.5 µM) + PEA (5.0 µM) | 42 |
| Compound of Example 3 (1.0 µM) + PEA (5.0 µM) | 22 |

Compound of Example 3 IC$_{50}$ = 0.9 µM
Compound of Example 3 + PEA (5.0 µM) IC$_{50}$ = 0.1 µM

EXAMPLE F

Effect of N-AVAM Molecules on Carrageenan-Mediated Oedema

Method:

The method described previously [materials and methods S. Mazzari et al. (1996) Europ. J. Pharmacol., 300: 227-236] were used for the purpose of evaluating the effects of N-AVAM molecules on the hyperreactivity of sensitive nerve cells.

The test compounds were administered orally suspended in physiological saline densified with CMC. The results are expressed as a percentage of variation in the volume of the paw relative to carrageenan.

Results:

| test compound | recording time in min. | | |
|---|---|---|---|
| | 60 | 120 | 180 |
| carrageenan | 100 | 100 | 100 |
| carrageenan + palmitoyl-ethanolamide (1 mg/kg, oral) | 85 | 78 | 70 |
| carrageenan + compound of Example 1 (5 mg/kg, oral) | 75 | 70 | 65 |
| carrageenan + palmitoyl-ethanolamide (1 mg/kg, oral) + Compound of Example 1 (5 mg/kg, oral) | 55 | 45 | 40 |

EXAMPLE G

Effect of N-AVAM Molecules on Carrageenan-Mediated Locomotor Hyperalgesia

Methods:

The method described previously [materials and methods S. Mazzari et al. (1996) Europ. J. Pharmacol., 300: 227–236] were used for the purpose of evaluating the effect of N-AVAM molecules on the hyperreactivity of sensitive nerve cells.

The test compounds were administered orally suspended in physiological saline densified with CMC. The results are expressed as a percentage of variation in the administered weight required to bring about a reduction in the size of the paw.

Results:

| Test compound | Recording times in min. | | | | | |
|---|---|---|---|---|---|---|
| | 0 | 60 | 120 | 180 | 240 | 300 |
| Vehicle | 100 | 71 | 64 | 50 | 48 | 52 |
| Palmitoylethanolamide (10 mg/kg, oral) | 100 | 82 | 80 | 76 | 64 | 66 |
| Compound of Example 1 (5 mg/kg, oral) | 100 | 80 | 72 | 65 | 58 | 64 |
| Palmitoylethanolamide (10 mg/kg, oral) + compound of Example 1 (5 mg/kg, oral) | 100 | 88 | 90 | 92 | 96 | 100 |

From the above results, it is seen that the compounds of the present invention can be used for the preparation of a medicinal product for human or animal use, by means of oral, parenteral, topical or transdermal administration.

As shown above, the compounds of the present invention can also be administered in combination with compounds which have agonist activity on the receptor CB2 of cannabinoids, with synergistic effect.

The compounds of the present invention can be used for the treatment of pathologies which are characterized and/or mediated by sensitization phenomena—NGF-mediated—of afferent nerve fibres, the said sensitization phenomena being in turn capable of giving rise to cell and tissue hyperreactivity at localized level. Thus, the compounds of formula (I) can be used for the treatment of pathologies characterized by a high degree of cell or tissue hyperreactivity mediated by supramaximal levels of NGF.

The definition given above is intended to refer, for example, to the following pathologies:

on the central nervous system, multiple sclerosis, amyotrophic lateral sclerosis, epilepsy, neurolathyrism, cranial trauma, spinal trauma, cerebral stroke, transient ischaemic attack, Huntington's chorea, Alzheimer's disease, primary dementia, dementia associated with viral pathologies, localized cytolytic pathologies associated with stress, tumour dissemination and proliferation pathologies associated with stress, heroin abstinence syndrome;

on the peripheral nervous system, peripheral, autonomic and somatic neuropathies, of traumatic, medicational, toxic, dysmetabolic or degenerative origin;

at the dermo-epidermal level and in the adjoining skin tissues, psoriasis, atopic dermatitis, heliodermatitis, actinic keratosis, seborrhoeic dermatitis, hypertrophic and cheloid cicatrization, scleroderma, dermatomyositis, polymyositis, pemphigus, pemphigoid, epidermolysis bullosa, urticaria-angioedema syndrome, balanitis, balanoposthitis, vulvitis, vulvar vestibulitis, folliculitis, seborrhoea, alopecia, seborrhoeic alopecia, ungual granuloma;

at the mucosal level, mucosal impairment of inflammatory nature in the mouth and of the gums, chronic inflammation of the gastrointestinal mucosae, pathologies mediated by hyperreactivity of the bladder mucosa and of the urinary, vaginal and vulvo-vaginal canals;

at the ocular level, traumatic and ulcerative corneal lesions, dry keratoconjunctivitis, Sjogren's syndrome, sympathetic ophthalmia, autoimmune uveitis, uveoretinitis, allergic conjunctivitis, ocular cicatritial pemphigoid, anoxo-ischaemic retinal diseases, glaucoma;

at the respiratory level, interstitial pulmonary fibrosis, bronchial asthma, chronic obstructive bronchopathy with an asthmatic component, allergic rhinitis;

at the cardiovascular level, cardiac reinfusion, atherosclerosis, heart attack, coronary restinosis after angioplasty;

at the osteoarticular level, chronic arthritis, rheumatic arthritis, psoriatic arthritis, erythromatous arthritis, systemic or discoid lupus, diseases caused by adverse changes in articular cartilage, osteoporosis;

at the level of the nociceptive system, pathologies involving impairment of nociception.

In addition, the compounds of formula (I) can be used as agents for blocking the proliferation of tumour cells, which is dependent on the presence of the prolactin receptor (rPRL), such as, for example, human breast and prostate tumour cells.

Thus, a subject of the present invention is the use of the compounds of the present invention, alone or in combination with a compound with agonist activity on the CB2 receptor of cannabinoids, for the preparation of a medicinal product for treating the pathologies mentioned above.

The therapeutically effective dose will vary depending on the mode of administration chosen, the seriousness of the pathology and the age, weight and state of health of the patient. Acceptable therapeutic doses of a compound according to the present invention can range in general from 0.1 to 20 mg/kg per day, with an administration regime which may include one or more daily doses and for a variable period, as will be determined by the treating physician based on his or her experience.

The pharmaceutical compositions according to the present invention can comprise, as active principle, one or more compounds of formula (I) mixed with suitable pharmaceutically acceptable excipients and diluents.

According to a further subject of the present invention, the pharmaceutical compositions can comprise one or more compounds of formula (I) together with one or more compounds of ALIAmide structure, mixed with suitable pharmaceutically acceptable excipients and diluents. The term "compounds of ALIAmide structure" means, for example, the compounds described in patent application EP 0 550 006 in the section entitled "DETAILED DESCRIPTION OF THE INVENTION", which is incorporated herein by reference.

Alternatively, the compounds of formula (I) and the ALIAmides may be prepared in pharmaceutically separate formulations, which may be used for simultaneous, sequential or separate administration of the two active principles.

In particular, the formulations for intravenous, subcutaneous or intramuscular administration will comprise solutions or suspensions suitable for injection.

The formulations for oral administration will comprise powders, granules, lozenges, pills and capsules.

The formulations for topical administration will comprise solutions, gels and ointments.

The pharmaceutical formulations are prepared in accordance with the usual methods used in the pharmaceutical field (mixing, dissolution, lyophilization, micronization, etc.), and as such will not be described in detail.

A further subject of the present invention is a kit for simultaneous, sequential or separate administration, comprising one or more compounds of formula (I), as defined in claim 1, and a compound with agonist activity on the CB2 receptor of cannabinoids, in suitable pharmaceutical formulations.

The present invention will now be further described by means of the chemical examples and pharmaceutical composition examples below.

CHEMICAL EXAMPLES

Example 1

Preparation of
N-(4-hydroxy-3-methoxybenzyl)oleylamide 2.83 g of oleic acid and 1.10 g of 4-methylmorpholine are dissolved in 30 ml of dimethylformamide at 0° C.; 1.44 g of isobutyl chloroformate are then added and the solution is stirred at 0° C. for 20 min.

1.90 g of 4-hydroxy-3-methoxybenzylamine hydrochloride and 1.10 g of 4-methylmorpholine are added to the solution thus obtained and the resulting mixture is stirred overnight at 0° C. 90 ml of water are then added and the resulting mixture is extracted 3 times with 40 ml of ethyl acetate. The organic phases are washed twice with 20 ml of 1N hydrochloric acid and twice with 15 ml of water; the organic phases are then combined, decolorized with animal charcoal, dried over anhydrous sodium sulphate and evaporated under vacuum.

The residue is purified by preparative chromatography in a column of silica gel, using a mixture of hexane/ethyl acetate/acetic acid in ratios of 70/30/0.5 as eluent; the eluate fractions containing the pure product are combined and evaporated to dryness, and the residue is finally dried under high vacuum.

The reaction yield is about 88%.

The physicochemical properties of the product N-(4-hydroxy-3-methoxybenzyl)oleylamide are as follows:
Physical state: whitish amorphous powder
Empirical formula: $C_{26}H_{43}NO_3$
Molecular weight: 417.64
Elemental analysis: C=74.78%; H=10.38%; N=3.35%; O=11.49%
Solubility in organic solvents: >10 mg/ml in DMSO; >10 mg/ml in ethanol
Solubility in water: sparingly soluble
TLC: 65/30/5 toluene/ethanol/acetic acid eluent; Rf=0.66

Example 2

Preparation of
N-(4-hydroxy-3-methoxybenzyl)-palmitoylamide 0.475 g of 4-hydroxy-3-methoxybenzylamine hydrochloride and 0.556 g of 4-methylmorpholine are dissolved in 10 ml of dimethylformamide at 0° C. A solution of 0.605 g of palmitoyl chloride in 5 ml of chloroform is added dropwise slowly over 30 min with continuous stirring.

The resulting mixture is stirred overnight at 0° C. and 25 ml of water are then added and this mixture is extracted 3 times with 10 ml of ethyl acetate.

The organic phases are washed twice with 5 ml of 1N hydrochloric acid and twice with 4 ml of water; the organic phases are then combined, decolorized with animal charcoal, dried over anhydrous sodium sulphate and evaporated under vacuum.

The residue is crystallized from 7 ml of tert-butyl methyl ether; the product, separated out by filtration, is washed twice with 3 ml of cold tert-butyl methyl ether and is finally dried under high vacuum.

The reaction yield is about 91%.

The physicochemical properties of the product N-(4-hydroxy-3-methoxybenzyl) palmitoylamide are as follows:
Physical state: white crystalline powder
Empirical formula: $C_{24}H_{41}NO_3$
Molecular weight: 391.60
Elemental analysis: C=73.61%; H=10.55%; N=3.58%; O=12.26%
Solubility in organic solvents: >10 mg/ml in DMSO; >10 mg/ml in ethanol
Solubility in water: sparingly soluble
TLC: 65/30/5 toluene/ethanol/acetic acid eluent; Rf=0.65

Example 3

Preparation of
N-(4-hydroxy-3-methoxybenzyl)-arachidonoylamide 304.5 mg of arachidonic acid and 110 mg of 4-methylmorpholine are dissolved in 5 ml of anhydrous dimethylformamide at 0° C. under an $N_2$ atmosphere.

144 mg of isobutyl chloroformate are then added and the solution is stirred at 0° C. for 20 min. 190 mg of 4-hydroxy-3-methoxybenzylamine hydrochloride and 110 mg of 4-methylmorpholine are added to the mixture thus obtained; this mixture is then stirred overnight at 0° C. 12 ml of cold water are then added and the resulting mixture is extracted 3 times with 4 ml of ethyl acetate.

The organic phases are washed twice with 2 ml of 1N hydrochloric acid, twice with 2 ml of water, twice with 2 ml of 5% $NaHCO_3$ solution and twice with 2 ml of water; the organic phases are then combined, decolorized with animal charcoal, dried over anhydrous sodium sulphate and evaporated to dryness under vacuum.

The residue is purified by preparative chromatography in a column of silica gel, using a 72/28/2 mixture of hexane/ethyl acetate/ethanol as eluent. The eluate fractions containing the pure product are combined and evaporated to dryness and the residue is finally dried under high vacuum and stored under $N_2$ at −20° C.

The reaction yield is about 82%.

The physicochemical properties of the product N-(4-hydroxy-3-methoxybenzyl) arachidonoylamide are as follows:
Physical state: whitish amorphous powder
Empirical formula: $C_{28}H_{41}NO_3$ Molecular weight: 439.64

Elemental analysis: C=76.5%; H=9.4%; N=3.19%; O=10.92%

Solubility in organic solvents: >10 mg/ml in DMSO >10 mg/ml in ethanol

Solubility in water: sparingly soluble

TLC: 65/30/5 toluene/ethanol/acetic acid eluent; Rf=0.68

Example 4

Preparation of N,N'-bis(4-hydroxy-3-methoxybenzyl)-nonanediamide 310 mg of 4-hydroxy-3-methoxybenzylamine free base are dissolved in 7 ml of anhydrous dimethylformamide at 0° C. under an $N_2$ atmosphere.

220 mg of 4-methylmorpholine and 225 mg of azelaoyl chloride dissolved in 3 ml of chloroform are then added, in this order, dropwise and slowly over 30 min while maintaining the temperature at 0° C.

The resulting mixture is stirred at 0° C. for 2 hours and then at room temperature for 6 hours. 20 ml of cold water are added and the mixture is extracted 3 times with 10 ml of ethyl acetate.

The organic phases are washed twice with 5 ml of 1N hydrochloric acid, twice with 5 ml of water, twice with 5 ml of 5% $NaHCO_3$ solution and twice with 5 ml of water; the organic phases are then combined, decolorized with animal charcoal, dried over anhydrous sodium sulphate and evaporated to dryness under vacuum.

The residue is purified by preparative chromatography in a column of silica gel, using a hexane/ethyl acetate/ethanol mixture in a gradient from the composition 70/30/5/0.1 to 30/55/15/0.1 as eluent. The eluate fractions containing the pure product are combined and evaporated to dryness, and the residue is finally dried under high vacuum.

The reaction yield is about 82%.

The physicochemical properties of the product N,N'-bis (4-hydroxy-3-methoxybenzyl) nonanediamide are as follows:

Physical state: whitish amorphous powder

Empirical formula: $C_{25}H_{34}N_2O_6$

Molecular weight: 458.56

Elemental analysis: C=65.48%; H=7.14%; N=6.11%; O=20.94%

Solubility in organic solvents: >10 mg/ml in DMSO

Solubility in water: sparingly soluble TLC: 65/30/5 toluene/ethanol/acetic acid eluent; Rf=0.37

EXAMPLES OF PHARMACEUTICAL FORMULATIONS

Example 5

Tablets

Each tablet contains:

| | |
|---|---|
| compound of Example 1 | 30 mg |
| lactose | 85 mg |
| corn starch | 75 mg |
| talc | 6 mg |
| magnesium stearate | 2 mg |
| carboxymethylcellulose | 2 mg |

Example 6

Soft Gelatin Capsules

Each capsule contains:

| | |
|---|---|
| compound of example 2 | 100 mg |
| plant oil | 100 mg |
| soybean lecithin | 20 mg |
| gelatin | 55 mg |
| glycerol | 15 mg |
| colorant E 127 | 0.1 mg |

Example 7

Tablets Containing Two Active Principles

Each tablet contains:

| | |
|---|---|
| compound of Example 3 | 30 mg |
| palmitoylethanolamide (micronized) | 30 mg |
| glycine | 70 mg |
| mannitol | 100 mg |
| microcrystalline cellulose | 18 mg |
| magnesium stearate | 2 mg |

Example 8

Gelatin Double-Operculum (A+B)

| | |
|---|---|
| each operculum of type A contains: | |
| compound of Example 1 (co-micronized with lactose) | 50 mg |
| lactose | 50 mg |
| sucrose | 93 mg |
| corn starch | 31 mg |
| magnesium stearate | 35 mg |
| povidone | 26 mg |
| monobasic potassium phosphate | 20 mg |
| cellulose acetate trimellitate | 95 mg |
| Each operculum of type B contains: | |
| palmitoylethanolamide (micronized) | 100 mg |
| sucrose | 93 mg |
| corn starch | 31 mg |
| magnesium stearate | 35 mg |
| povidone | 26 mg |
| monobasic potassium phosphate | 20 mg |
| cellulose phosphate trimellitate | 95 mg |

Example 9

Lyophilized Vials

Each lyophilized vial contains:

| | |
|---|---|
| compound of Example 3 (co-micronized with mannitol) | 50 mg |
| mannitol | 75 mg |

-continued

Each solvent vial contains:

| | |
|---|---|
| soybean lecithin | 30 mg |
| apyrogenic double-distilled water q.s. | 2 ml |

Example 10

Aerosol

Each dosed aerosol can contains:

| | |
|---|---|
| compound of Example 2 | 10 mg |
| sorbitan trioleate | 50 mg |
| trichloromonofluoromethane | 200 mg |
| dichlorodifluoromethane | 200 mg |

Example 11

Suppositories Containing Two Active Principles

Each suppository contains:

| | |
|---|---|
| compound of Example 3 | 100 mg |
| azelaic acid diethanolamide | 100 mg |
| semisynthetic glycerides | 2 g |

Example 12

Vaginal Gel Containing Two Active Principles 100 g of vaginal gel contain:

| | |
|---|---|
| compound of example 2 | 150 mg |
| azelaic acid diethanolamide | 1 g |
| sodium hyaluronate | 100 mg |
| sodium alginate | 2.5 g |
| glycerol | 5 g |
| bronopol | 300 mg |
| demineralized water q.s. | 100 g |

Example 13

Dermatological Cream 100 g of cream contain:

| | |
|---|---|
| compound of example 4 | 200 mg |
| sorbitan monostearate | 500 mg |
| polyoxyethylene sorbitan monostearate | 3 g |
| stearic acid | 3 g |
| liquid petroleum jelly | 15 g |
| methyl para-hydroxybenzoate | 0.2 g |
| ethyl para-hydroxybenzoate | 0.05 g |
| demineralized water q.s. | 100 g |

Example 14

Hair Lotion 100 g of hair lotion contain:

| | |
|---|---|
| compound of Example 4 | 1000 mg |
| trans-traumatic acid diethanolamide | 200 mg |
| propylene glycol | 25 g |
| ethyl alcohol | 50 g |
| demineralized water q.s. | 100 g |

Example 15

Ointment for Ocular Use 100 g of ointment contain:

| | |
|---|---|
| compound of Example 2 | 500 mg |
| fluid petroleum jelly q.s. | 100 g |

Example 16

Mouthwash for Oral Use 100 g of mouth wash contain:

| | |
|---|---|
| compound of Example 3 | 700 mg |
| azelaic acid diethanolamide | 1 g |
| glycerol | 40 g |
| ethyl alcohol | 20 g |
| mint flavouring | 2 g |
| saccharin | 100 mg |
| methyl p-hydroxybenzoate | 0.3 g |
| ethyl p-hydroxybenzoate | 0.08 g |
| demineralized water q.s. | ad 100 g |

Example 17

Gel for Oral Use 100 g of gel contain:

| | |
|---|---|
| compound of Example 1 | 1200 mg |
| sodium hyaluronate | 200 mg |
| carbomer | 300 mg |
| sorbitol | 20 g |
| methyl p-hydroxybenzoate | 0.2 g |
| ethyl p-hydroxybenzoate | 0.05 g |
| mint flavouring | 1 g |
| demineralized water q.s. | 100 g |

Example 18

Fluid Gel Oil for Otological Use 100 g of fluid gel contain:

| | |
|---|---|
| compound of Example 2 | 150 mg |
| gel oil | 80 mg |
| plant oil | q.s. 100 g |

The invention claimed is:

1. A method of treating a condition selected from the group consisting of breast tumor and prostate carcinoma, said method comprising administering a compound selected from the group consisting of:

N-(4-hydroxy-3-methoxybenzyl)oleylamide;

N-(4-hydroxy-3-methoxybenzyl)palmitoylamide;

N-(4-hydroxy-3-methoxybenzyl)arachidonoylamide; and

N,N'-bis(4-hydroxy-3-methoxybenzyl)nonanediamide.

* * * * *